(12) United States Patent
Fontaine et al.

(10) Patent No.: US 9,588,056 B2
(45) Date of Patent: Mar. 7, 2017

(54) METHOD FOR PARTICLE DETECTION ON FLEXIBLE SUBSTRATES

(71) Applicant: Corning Incorporated, Corning, NY (US)

(72) Inventors: Norman Henry Fontaine, Painted Post, NY (US); Alana Marie Whittier, Painted Post, NY (US)

(73) Assignee: CORNING INCORPORATED, Corning, NY (US)

(*) Notice: Subject to any disclaimer, the term of this patent is extended or adjusted under 35 U.S.C. 154(b) by 0 days.

(21) Appl. No.: 14/722,478

(22) Filed: May 27, 2015

(65) Prior Publication Data
US 2015/0346109 A1    Dec. 3, 2015

Related U.S. Application Data

(60) Provisional application No. 62/004,498, filed on May 29, 2014.

(51) Int. Cl.
| | |
|---|---|
| *G01N 21/00* | (2006.01) |
| *G01N 21/89* | (2006.01) |
| *G01N 21/896* | (2006.01) |
| *G01N 21/94* | (2006.01) |
| *G01N 21/958* | (2006.01) |
| *G01N 21/84* | (2006.01) |
| *G01N 21/47* | (2006.01) |

(52) U.S. Cl.
CPC ......... *G01N 21/8914* (2013.01); *G01N 21/89* (2013.01); *G01N 21/8901* (2013.01); *G01N 21/896* (2013.01); *G01N 21/94* (2013.01); *G01N 21/958* (2013.01); *G01N 2021/4707* (2013.01); *G01N 2021/845* (2013.01); *G01N 2021/8965* (2013.01); *G01N 2021/8967* (2013.01); *G01N 2021/945* (2013.01); *G01N 2201/06113* (2013.01)

(58) Field of Classification Search
CPC .............................. G01N 21/00; G01N 33/00
USPC .......................... 356/237.2–237.6, 364, 338
See application file for complete search history.

(56) References Cited

U.S. PATENT DOCUMENTS

| | | | |
|---|---|---|---|
| 4,402,607 A | | 9/1983 | McVay et al. |
| 4,410,278 A | * | 10/1983 | Makihira ............. G01N 21/952 |
| | | | 250/559.07 |
| 4,671,663 A | | 6/1987 | Sick |

(Continued)

FOREIGN PATENT DOCUMENTS

| | | |
|---|---|---|
| DE | 3643297 A1 | 6/1988 |
| JP | 07190942 A | 7/1995 |

(Continued)

OTHER PUBLICATIONS

European Patent Office; International Search Report; Mail Date: Sep. 9, 2015; pp. 1-4.

(Continued)

*Primary Examiner* — Tarifur Chowdhury
*Assistant Examiner* — Isiaka Akanbi
(74) *Attorney, Agent, or Firm* — Kevin M. Able

(57) ABSTRACT

Methods for detection of particulate on thin, flexible substrates wherein the substrate is positioned in a bend comprising an apex line. The apex line is illuminated by grazing angle illumination, and light from the illumination scattered by the particulate is captured by a detection apparatus.

18 Claims, 10 Drawing Sheets

(56) References Cited

U.S. PATENT DOCUMENTS

| | | | | |
|---|---|---|---|---|
| 5,251,010 A | * | 10/1993 | Maltby, Jr. | G01B 11/306 250/559.45 |
| 5,317,380 A | | 5/1994 | Allemand | |
| 6,301,059 B1 | * | 10/2001 | Huang | G02B 27/0025 359/668 |
| 6,449,035 B1 | | 9/2002 | Batchelder | |
| 6,532,065 B1 | | 3/2003 | Grimme et al. | |
| 7,385,710 B1 | * | 6/2008 | Sturgill | G01B 11/06 356/632 |
| 7,929,129 B2 | | 4/2011 | Berg et al. | |
| 9,255,893 B2 | * | 2/2016 | Grzegorczyk | H04N 7/183 |
| 2004/0202418 A1 | * | 10/2004 | Ghiron | G02B 6/34 385/36 |
| 2005/0285059 A1 | | 12/2005 | Gerber et al. | |
| 2011/0242537 A1 | | 10/2011 | Shigeta et al. | |
| 2013/0112667 A1 | * | 5/2013 | Holmgren | H01L 21/268 219/121.6 |
| 2013/0215923 A1 | * | 8/2013 | Cobb | G02B 27/0927 372/49.01 |
| 2014/0347664 A1 | | 11/2014 | Schrader et al. | |

FOREIGN PATENT DOCUMENTS

| | | |
|---|---|---|
| JP | 2008107131 A | 5/2008 |
| JP | 2008107132 A | 5/2008 |
| JP | 2008256539 A | 10/2008 |

OTHER PUBLICATIONS

Lilienfeld; "Optical Detection of Particle Contamination on Surfaces: A Review"; Aerosol Science and Technology 5 (1886); pp. 145-165.

Hayashi; "P-27: Next Generation Particle Inspection System "HS-730" for FPD Glass Plates"; SID 02 Digest (2002); pp. 300-303.

H.C. van de Hulst; "Light Scattering by Small Particles" Copyright 1957; Chapter 2, Section 2.4 Efficiency Factors; p. 14.

From: www.toray-eng.com/lcd/inspection/lineup/hs-830.html; Article: HS-830 Foreign Matter Inspection Device for FPDS. Toray Engineering, 3 pages.

\* cited by examiner

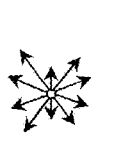
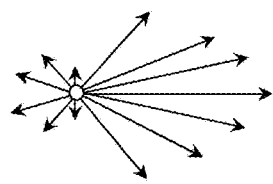
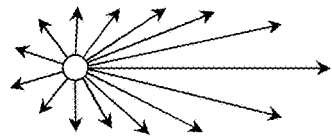
FIG. 1A      FIG. 1B      FIG. 1C
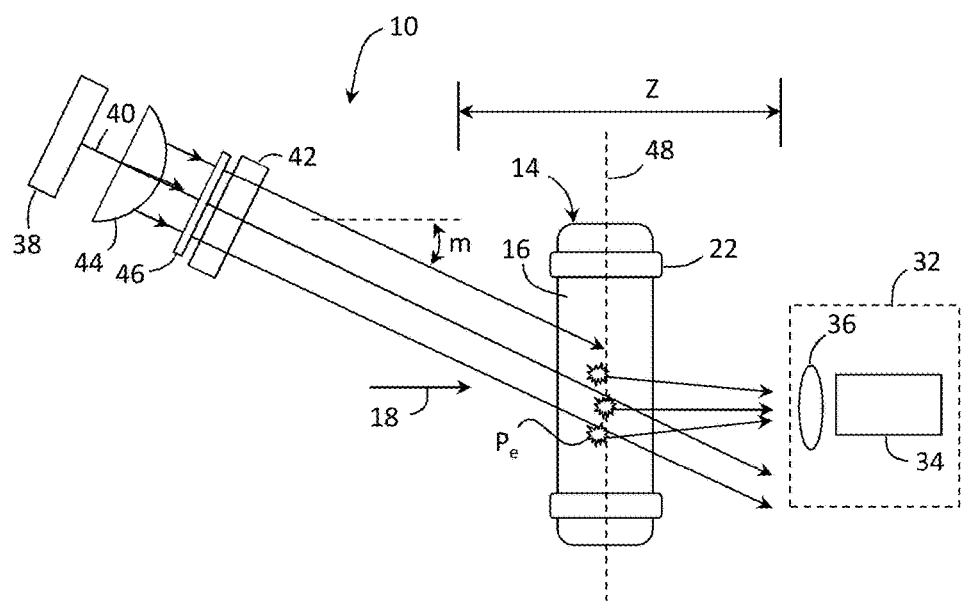
FIG. 2

METHOD FOR PARTICLE DETECTION ON FLEXIBLE SUBSTRATES

CROSS-REFERENCE TO RELATED APPLICATIONS

This application claims the benefit of priority under 35 U.S.C. §119 of U.S. Provisional Application Ser. No. 62/004,498 filed on May 29, 2014, the content of which is relied upon and incorporated herein by reference in its entirety.

BACKGROUND

Field

The present invention relates generally to a method for detecting particulate on a substrate, and in particular a method to detect and measure particulate on thin, flexible substrates such as glass sheets or ribbons.

Technical Background

High speed, non-contact methods are needed to identify the occurrence, the locations, the number, the sizes and/or the types of particulates on the surfaces of thin and flexible glass substrates, such as glass sheets or glass ribbons as may be useful for display or other electronic applications. As used herein, the term glass refers typically to silica-based inorganic glasses, but can also refer to non-silica-based glasses, or glasses formed by organic compounds. While glass sheets may be flat and small in size, glass ribbons can be hundreds of meters long, a meter or more wide and suitable for winding onto or unwinding from spools. If particulates on the surface can be detected and identified during substrate manufacturing, then steps can be taken to address the source of the particulates and, if necessary, to clean away the particulates in a downstream process. This can reduce waste material, increase production rates and decrease re-working and cleaning costs. In some products that use the glass as a laminate component, a particle only one micrometer (μm) or less in size can be sufficient to interfere with the bond between the laminated layers. Thus, particles that escape detection can create loss of raw material, add to handling expense and lower the yield of good product for other manufacturers that use the glass as a sub-component.

SUMMARY

In accordance with the present disclosure a grazing incidence and detection method is described that is suitable for inspecting flexible substrates for particle contamination. These substrates can be individual sheets, or ribbons having a length as much as hundreds of meters and meters wide. The method is capable of distinguishing which side of the substrate particles lie upon while the substrate is in continuous motion. By bending the flexible substrate over a roller or air-bearing, numerous advantages can be obtained for particle contaminate screening, including: the bending of the substrate forms an arch, which creates a self-supporting structure that will in certain embodiments hold its shape and position in the vicinity of an apex region without the need for contact points or other supporting structures; the bending of the substrate ensures the apex line (where the measurement occurs) will not sag out of the focal plane of the illumination or the detection systems; the method exposes the apex of the exterior side of the substrate bend as a well-defined and stationary line of maximum displacement about which a fixed optical grazing incidence and forward-scattering detection screening system may be designed; since the substrate bends out of the way, the optical axes of the illumination and detection system can be placed at an angle within 10 degrees or less of a plane tangent to the apex line and the physical extent of the components can extend below the tangent plane of the glass surface at the measurement location, eliminating the need for mirrors to redirect the grazing illumination to the screening area on the substrate or the scattered light from the particles to the detection area; the grazing incidence and detection occurs at very high angles and on the same side of the substrate, which greatly diminishes the illumination and detection of scattering from particles on the opposite side of the substrate when the substrate is transparent, generally at ratios of 3800:1; the method will work for very thin substrates, for example between 25 μm to 300 μm in thickness; the bending allows the grazing incidence and detection system to be placed in very close proximity to the apex line, which allows the use of lower cost, shorter working distance and/or higher magnification optical illumination and detection systems with good spatial resolution and particle location ability; the substrate can be moved through the inspection area continuously and at high speed to inspect a large fraction of a surface of the substrate, or even an entire surface, without cutting the substrate and without manual handling; it is easy to discriminate which side of the substrate a particle resides upon by combining two such systems in series, whereby the flexible substrate is bent around two support devices, with one bend exposing an apex line for one surface and the other bend exposing an apex line for the opposite surface; the same inspection system method and hardware can be multiplexed to allow simultaneous inspection across the full width of the substrate without size limitations; the system does not require a separate large and precise positioning equipment system for the movement of the substrate or the optical inspection system during a measurement; the measurement system can be made small and light weight, and can be designed to be dis-mounted and re-mounted at any support device location in a spooling or re-spooling process where screening for contamination may be needed.

Accordingly, in one embodiment, a method for detecting particulate on a substrate is disclosed comprising conveying the substrate over an arcuate surface and producing a first bend in at least a portion of the glass substrate. The method further comprises illuminating an exterior surface of the substrate at an apex line of the first bend with a laser beam, wherein a central axis of the laser beam is within 10 degrees of a plane tangent to the apex line and the laser beam is elongated in a direction perpendicular to the central axis, the illumination producing scattered light from particulate on the exterior surface at the apex line, and detecting the scattered light with a detection device, wherein an optical axis of the detection device is within 10 degrees of the tangent plane at the apex line.

The conveying may comprise, for example, conveying the substrate over a roller, and may further comprise contacting edge portions of the substrate with spacers positioned on the roller and configured to space the substrate above a surface of the roller.

In some embodiments the conveying may comprise conveying the substrate over an air bearing to produce the first bend.

The method can include directing the laser beam through a slow-axis cylindrical lens, and may further comprise directing the laser beam through a fast-axis cylindrical lens.

A meridional angle m of the central axis in the tangent plane containing the apex line can be in a range from 6 degrees to 30 degrees during the illuminating.

In some embodiments the substrate may be a glass substrate. The glass substrate may be a glass ribbon or a glass sheet. In other embodiments the substrate may be a polymer substrate, such as a plastic film or other polymer sheet or ribbon.

The method may further comprise conveying the glass substrate over a second arcuate surface and producing a second bend in at least a portion of the glass substrate such that the exterior surface of the first bend is an interior surface of the second bend.

The method may further comprise acquiring a series of images of the scattered light during the conveying and using the images to determine at least one of the location of the particulate, the size of the particulate, or the number of particulate In another aspect a method of detecting particulate on a surface of a glass substrate is described comprising conveying a glass substrate over an arcuate surface and producing a bend in at least a portion of the glass substrate. The method may further comprise illuminating an exterior surface of the glass substrate at an apex line of the bend with a laser beam, wherein a central axis of the laser beam is within 10 degrees of a plane tangent to the apex line and the laser beam is elongated in a direction perpendicular to the central axis, the illumination producing scattered light from particulate on the exterior surface at the apex line, and detecting the scattered light with a detection device, wherein an optical axis of the detection device is within 10 degrees of the tangent plane at the apex line.

The glass substrate may be, for example, a glass ribbon wherein the conveying comprises unspooling the glass ribbon from a spool prior to the illuminating. The conveying may comprise spooling the glass ribbon onto a spool after the illuminating. The conveying may comprise conveying the glass substrate over a second arcuate surface and producing a second bend in at least a portion of the glass substrate such that the exterior surface of the first bend is an interior surface of the second bend.

The method may further comprise illuminating an exterior surface of the glass ribbon at an apex line of the second bend with a second laser beam, wherein a central axis of the second laser beam is within 10 degrees of a plane tangent to the apex line of the second bend and the second laser beam is elongated in a direction perpendicular to the central axis of the second laser beam, the illuminating producing scattered light from particulate on the exterior surface of the second bend at the apex line of the second bend.

The methods disclosed herein can be used on large and small sheets that are individual pieces of glass, or on a glass ribbon in a continuous and un-interrupted fashion and the glass ribbon is spooled or re-spooled onto rolls.

High speed line-scan cameras can be used for inspection. The narrow height of the line scan camera's imaging area increases read-out speed and the long width of the camera's imaging area allows it to observe a wider width of the sheet for a given number of pixels than do area scan cameras. This allows for faster production speeds and makes the method very amenable to a continuous and high speed process because the substrate, e.g. glass ribbon, is already moving through the measuring area on a conveyer.

Because the optical system can be bolted directly onto a roller or air-bearing and moved wherever it is needed, the method eliminates the need for a separate optical screening system or screening area in a production setting.

Cameras with differing detection angles can be used in tandem to obtain more information or to screen for directional scattering from particle faces. This includes in-plane of incidence and out-of-plane of incidence scattering.

Additional features and advantages of the present disclosure will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description present embodiments of the disclosure, and are intended to provide an overview or framework for understanding the nature of the disclosure and the embodiments as they are claimed. The accompanying drawings are included to provide a further understanding of the disclosure, and are incorporated into and constitute a part of this specification. The drawings illustrate various embodiments of the disclosure, and together with the description serve to explain the principles and operations thereof.

BRIEF DESCRIPTION OF THE DRAWINGS

FIGS. 1A-1C are schematic views depicting qualitatively the scattering of light from a particle of different size, increasing in size from left to right;

FIG. 2 is a top view of an apparatus for detecting particulate on a thin, flexible substrate according to an embodiment of the present disclosure;

DETAILED DESCRIPTION

Figure 3:
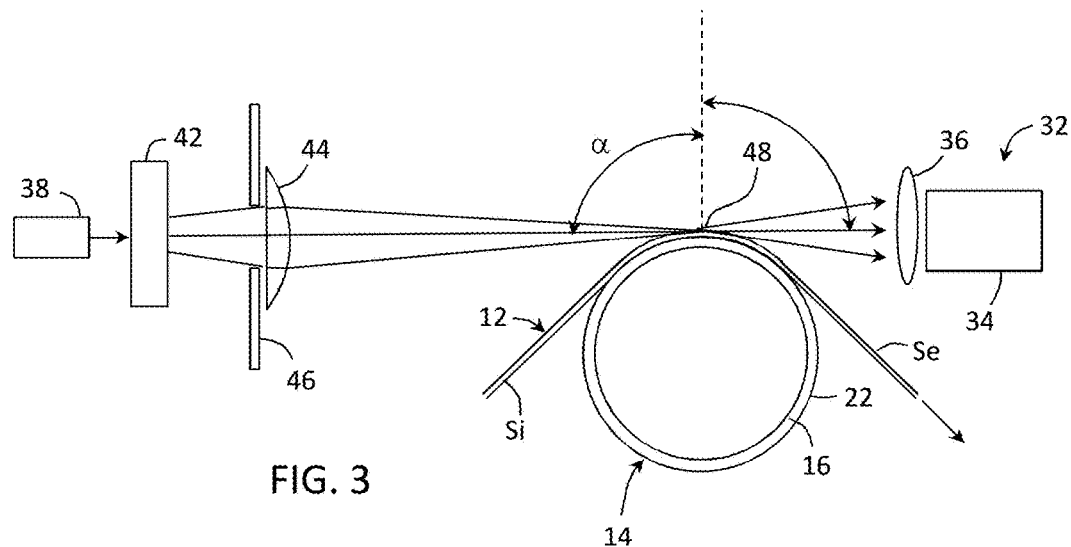
FIG. 3 is a side view of the apparatus of FIG. 2.

The following disclosure describes embodiments in the context of individual glass sheets and/or long glass ribbons, although the apparatus and methods described herein may be used to detect and/or characterize particulate contamination of other sheet or ribbon media such as polymer media.

Reference will now be made in detail to embodiments of the disclosure, examples of which are illustrated in the accompanying drawings. Whenever possible, the same reference numerals will be used throughout the drawings to refer to the same or like parts.

As used herein, the singular forms "a," "an" and "the" include plural referents unless the context clearly dictates otherwise. Thus, for example, reference to a "support device" includes aspects having two or more such support devices, unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. When ranges are expressed as "between" one value and another value, the one value and the other value represent the endpoints of the range and are included within the range.

As used herein, the terms "having" and "including" are open ended and do not preclude the presence of other properties, characteristics, attributes or elements, unless specifically stated.

Optically based particle screening systems for use on generally planar substrates can include several basic requirements for illumination and detection sub-systems. The light that impinges on the substrate should subject particles everywhere on the substrate surface with nearly the same irradiance and radiant intensity across the entire face of the substrate to ensure all particles are illuminated in the same way as they are being measured. Similarly, the detection system should receive light scattered by particles with uniform aperture across the field of view. It is difficult and expensive to construct fixed optical systems that can illuminate or image the face of a large flat substrate, such as a glass substrate, uniformly. As a result, scanning systems are often employed to screen a smaller portion of a large substrate at any one time and then stitch the results together to achieve coverage over a large area. This requires the use of large, precise motion control systems that are expensive and difficult to implement.

It takes a relatively long time to measure large substrates with current technology, for example long lengths of a glass ribbon that may be a meter or more in width and tens, or even hundreds of meters long. For individual substrates, each substrate must be cut to size and loaded into the measurement system prior to measurement. As such, many machines and operators are needed to measure (screen) a large fraction of the substrate of many parts in a timely manner. Spooling can be a benefit for both the manufacturer and the customer of flexible glass ribbons because spooling facilitates shipping, handling and storage. However, cutting the substrate for inspection may preclude subsequent spooling of the product in the instance where the substrate comprises a thin glass ribbon. One alternative to full inspection is to use a low-fraction sampling method to test a predetermined percentage of a substrate and/or sub-areas of the substrate. Another alternative is to test a percentage of the substrates and not the entire lot. This may be undesirable because there is always a risk that contaminating particles may be missed on untested areas and untested substrates. If the process is working well, particulates will be small and sparsely distributed across a substrate, which makes their optical detection more difficult. Hence, ensuring that each of the substrates are of the highest quality necessitates measuring as much of each substrate as possible at the highest possible sampling density.

It is helpful, particularly but not exclusively for transparent substrates, if one can also identify both the side of the substrate where the contaminants reside and the particle sizes because steps can then be taken to ensure the cleanest side is used as the contact surface for any subsequently bonded component that must touch the glass. Knowing which side has the contaminant and identifying its size may also help when finding sources of contamination that occur during manufacturing and handling of the substrate. For substrates having a thickness greater than about 300 micrometers ($\mu m$), determining on which side a particulate may reside can be accomplished by ensuring one surface is in the object plane of the optics for the detection system and the other surface is not.

As glass substrates become larger (e.g. meters wide and tens or hundreds of meters long) and thinner (e.g., 300 micrometers and less), it becomes more difficult to use some of the currently available optical inspection methods to identify which surface of the glass a contaminant may reside on and to identify the contamination type. When the detection system is viewing a large and very thin glass substrate, from a direction normal to a first surface of the glass substrate, for example a glass substrate with a thickness in a range from about 25 micrometers to about 300 micrometers, both surfaces of the glass substrate will be near the focal plane of the detection system at the same time. Thus, if the glass substrate is transparent, light scattered from particles on the opposite surface can be sufficiently strong and well-imaged to confuse the surface and size determination for the contaminant. Thin glass substrates have an additional problem because the thin substrate can bend and sag, leaving various sections of the glass substrate in or out of the plane of focus. Hence, light scattered from particles on either the first and/or second surface of the glass substrate may be imaged onto the detector system. In a static measurement, one can attempt to position the thin glass substrate onto precisely constructed contact pins to ensure the entire surface of the glass substrate is flat. However, this may not be desirable because the contact points at the pins create a source of particle contamination to the surface and may themselves produce scratches in the surface. Furthermore, when measuring near the contact points, exclusion zones are required for analyzing the data near the pins to avoid counting the point the sheet rests upon as particle contamination. This makes it possible to miss detection of particle contaminants in those regions. Moreover, a higher density of contact pins are needed to minimize sagging as the substrate becomes thinner, thereby increasing the foregoing limitations.

Once the particle object size becomes smaller than the spatial resolution of the camera (or other spatially resolving detection system), one cannot use the size of the object in the image to estimate the particle sizes. Frequently, the integrated intensity of the light is used for estimating particles with a size less than the spatial resolution limit of the detection system. For micrometer-sized particles and larger, basic scattering theory shows that the total scattering of the optical illumination by a particle generally decreases by a factor that is in proportion to the cross-sectional area the particle presents to the illuminating light beam. Thus, a particle that is $1/10^{th}$ the diameter of another, similar particle, will scatter 100 times less light in total than the similar particle. In addition, the scattering will be non-isotropic. Mie scattering theory shows that micrometer and sub-micrometer sized spherical particles can scatter visible light more strongly in specific directions compared to other directions and this scattering depends on the angle of illumination, incident polarization, particle material composition and particle size. This angular and polarization-dependent scattering can be quite variable with small changes in particle size when that size approaches the range of roughly $1/20^{th}$ to 20 times the wavelength $\lambda$ of the illumination. FIGS. 1A-1C provide a qualitative sense of the scattering amplitude for small, spherical particles, where the length and direction of the illustrated vectors provide an indication of the relative strength of the scattering amplitude along the shown direction. Roughly categorized, FIG. 1A illustrates scattering for a spherical particle with a diameter d much less than the wavelength $\lambda$ of the incident light, FIG. 1B illustrates scattering for a spherical particle with a diameter d, where $\lambda/20 \leq d < 20\lambda$ and FIG. 1C illustrates scattering for a spherical particle with a diameter d equal to or greater than 20 times the wavelength of the incident light. For each of FIGS. 1A-1C, the incident illumination is from left to right.

For non-spherical particles, particle shape can also factor into the directionality of scattering. For symmetric particles and randomly oriented non-symmetric particles the scattering into the forward direction is generally the strongest and can be orders of magnitude stronger than the light scattered into other angles.

A number of approaches have been used to detect particles on flat glass surfaces. Some systems use a high angle of incidence illumination (roughly 70 degrees from the surface normal) and detect the back-scattered light normal to the surface. Such particle detection systems can measure flat glass substrates with dimensions on the order of 2 meters per side and can detect particle sizes as small as 0.3 to 1.0 micrometers (μm). These systems often use support pins to keep thin substrates flat and employ scanning techniques to measure large pieces.

Detection of small particles on a surface can be achieved by shining light through the substrate from a direction normal to the surface of the substrate and detecting scattering from a near-normal angle, but outside of the numerical aperture of the illuminating beam (in the dark field). Similarly, the detection could be at a normal incidence and the illumination directed at near-normal incidence, but outside the aperture of the detection system. However, if one also requires the ability to discriminate which surface of the glass substrate the particle resides on for thin glass substrates, the aforementioned issues related to both surfaces being near focus, sheet sagging and the presence of contact pins make this near normal incidence—near normal detection, forward scattering approach less than ideal.

It is difficult to design a grazing incidence, low-angle forward scattering screening system that can detect and locate particles on large area glass substrates, particularly when they are thin and transparent. For example, glass sheets, or glass ribbons contemplated by the present disclosure may comprise a thickness equal to or less than about 300 micrometers, such as in a range from about 25 micrometers to about 300 micrometers, from about 25 micrometers to about 200 micrometers, from about 25 micrometers to about 100 micrometers or from about 25 micrometers to about 50 micrometers or within any range of thicknesses between 25 micrometers and 300 micrometers. Such glass sheets, or glass ribbons, may have a width equal to or greater than 0.5 meters, equal to or greater than 1 meter, and in some instances a width of the glass sheet or glass ribbon may be equal to or greater than 2 meters. The primary problem encountered during the contemplated measurement is that of relaying an incident beam to a surface of the substrate and receiving the scattered light while simultaneously trying to achieve a condition whereby both lights, the illumination light and the measured forward scattered light, are propagating as nearly parallel to the surface of the substrate as possible. Such a system must also reject specularly reflected light from the illuminated surface of the substrate and all other light that is not due to scattering from the particle(s). One method would be to place the optical illumination and detections systems outside the periphery of the substrate and use long focal length optical components to direct the optical axis of the illuminating beam to the measurement point on the substrate surface, and to then collect the scattered light. Implemented in that manner, portions of the housings in those systems can lie below the plane of the substrate. However, as the illumination and detection angles approaches 90° from the surface normal, it becomes very difficult to design an optical system that maintains uniform illumination and detection efficiencies across the required working distances of a large substrate. Another method is to use mirrors positioned very close to the substrate surface to re-direct the illumination onto the surface and to direct the scattered light into detectors. This simplifies the optical design because the working distances can be shorter. Such an arrangement can be put into an optical head assembly located above the substrate and configured to scan across the substrate, or the substrate can be moved underneath a fixed optical head. The substrate must be kept locally flat to allow the optical head to be as close to the substrate surface as possible without contacting the surface, and for the optical illumination and detection systems to remain in good focus.

Figure 4:
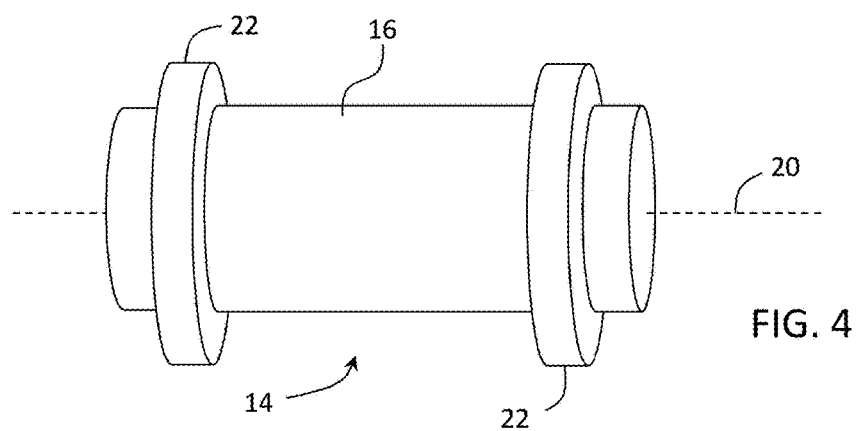
FIG. 4 is a perspective view of a cylindrical support device according to an embodiment of the present disclosure.

Referring now to FIGS. 2 and 3, an example apparatus 10 for detecting a particle $P_e$ on an exterior surface $S_e$ of a flexible, inorganic glass ribbon 12 is shown comprising a support device 14 comprising an arcuate surface 16 with a radius of curvature. The glass ribbon 12 may be transparent or opaque, but for the purpose of the present discussion is assumed to be visibly transparent. The glass ribbon is transported by transport devices (not shown) in a conveyance direction 18 over arcuate surface 16, such as by pinch rollers configured to grip edge portions of the glass ribbon, so that at least a portion of glass ribbon 12 adjacent to the arcuate surface 16 comprises a bend radius (radius of curvature). Arcuate surface 16 may have a constant radius of curvature, or arcuate surface 16 may have a radius of curvature that varies. Accordingly, the glass ribbon may also have a radius of curvature in the conveyance direction that varies. Support device 14 may be, for example, a cylinder, such as a right angle circular cylinder as shown in FIGS. 2 and 3, or support device 14 may be a portion of a cylinder. In some embodiments, such as the embodiment of FIG. 4, support device 14 may be a roller configured to rotate about an axis of rotation 20, which coincides with a longitudinal axis of the roller. The embodiment of a support device 14 configured as a cylindrical roller in FIG. 4 includes spacers 22 that contact the glass ribbon and position the glass ribbon adjacent to but spaced apart from arcuate surface 16 of support device 14. Spacers 22 may be located on support device 14 so that spacers 22 contact only edge portions of the glass ribbon and do not contact a central portion of the glass ribbon, thereby preventing the glass ribbon from contacting the arcuate surface 16. Spacers 22 may be, for example, formed from a resilient material to prevent damage to the glass ribbon. For example, spacers 22 may be "O"-rings positioned at or proximate to the ends of the roller.

Figure 5:
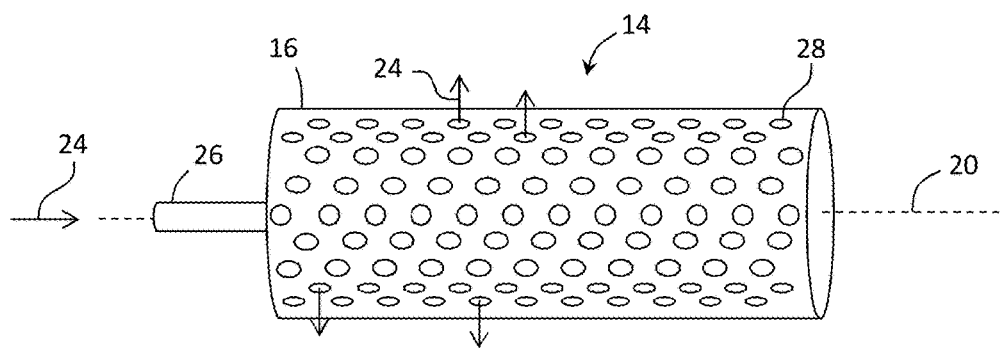
FIG. 5 is a perspective view of a porous cylindrical support device according to another embodiment of the present disclosure.

In another embodiment, depicted in FIG. 5, an example support device 14 is shown that may or may not be configured to rotate. The support device 14 of FIG. 5 includes an arcuate surface 16 that is porous and over which the glass ribbon is conveyed so that at least a portion of the glass ribbon comprises a radius of curvature. A fluid 24 (e.g. a gas) is supplied to an interior of the support device from a fluid supply (not shown) through supply pipe 26. While fluid supply pipe 26 is shown entering support device 14 through an end thereof, fluid supply pipe can be connected in support device 14 in any suitable way that does not interfere with conveyance of the glass ribbon. The interior of support device 14 is in fluid communication with pores 28 of the porous arcuate surface 16, and fluid 24 exiting the pores supporting the glass ribbon such that the portion of the glass ribbon that is adjacent to but spaced apart from the arcuate surface 16, thus creating a radius of curvature in the ribbon while making no contact with the arcuate surface.

Figure 6:
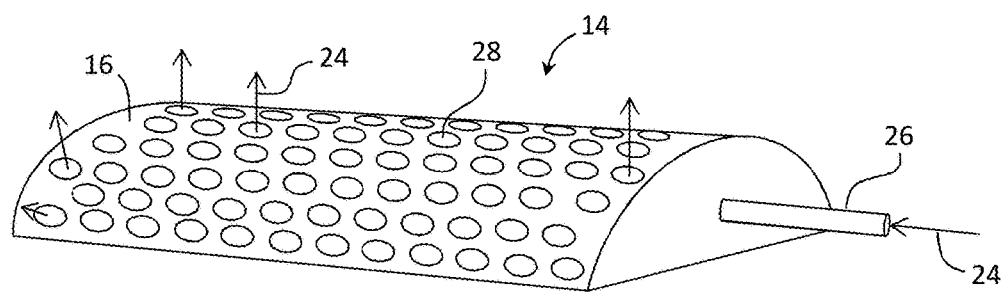
FIG. 6 is a perspective view of a porous support device according to another embodiment of the present disclosure.

In another embodiment shown in FIG. 6, a support device 14 forming only a portion of a cylinder is shown and may be employed. The radius of curvature for arcuate surface 16 in accordance with FIG. 6 may, in some embodiments, be constant, while in other embodiments the radius of curvature of arcuate surface may vary along conveyance direction 18 and around the curvature of the support device 14.

Figure 7:
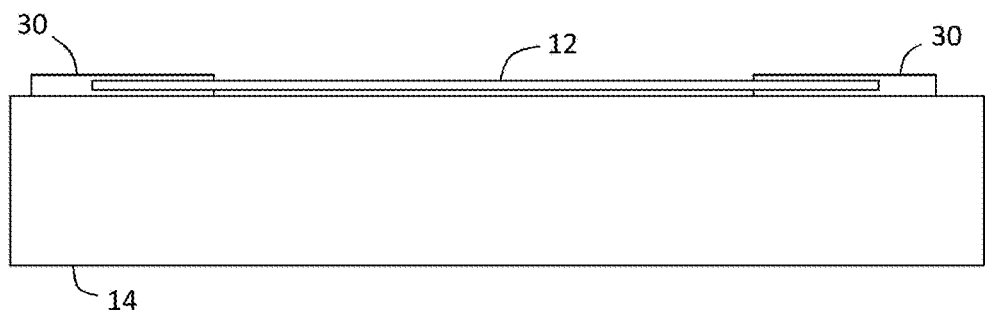
FIG. 7 is a cross sectional view of a substrate with supporting edge tabs and positioned over a support device.

Turning to FIG. 7, in some embodiments, glass ribbon 12 may include an edge tab 30, which, as used herein, refers to a material applied to an edge portion of the glass ribbon to protect the vulnerable edges of the ribbon. The edge tab may extend beyond the edge of the glass ribbon and serve as a handling tab that prevents direct contact with the rest of the surface of the glass ribbon. The edge tab may be, for example, a polymer tape, e.g. Kapton® tape, applied to an edge portion of the glass ribbon. The edge tab may be applied to only one side of the glass ribbon, or to both sides, and may be applied to one edge portion of the glass ribbon or to both edge portions of the glass ribbon. In instances where edge tabs have been applied to the edge portions of the glass ribbon, the glass ribbon may be conveyed directly on a roller-style support device 14 without the need for spacers on the support device, wherein the edge tab contacts the roller and serves to space the glass ribbon apart from the arcuate surface of the roller and thereby prevent contact between the glass and the arcuate surface.

Figure 8:
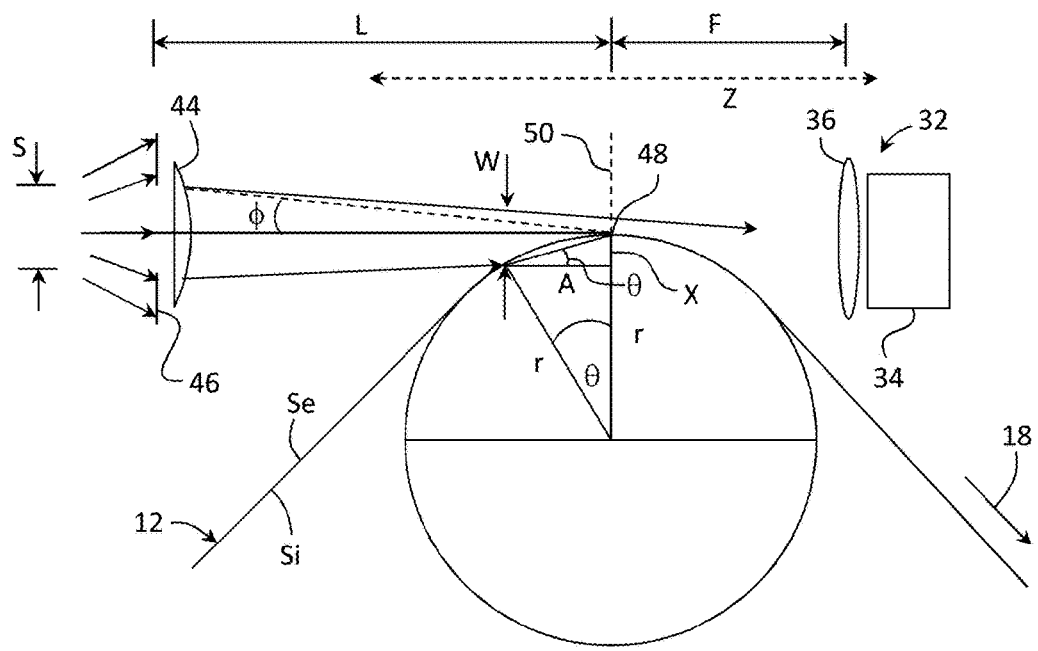
FIG. 8 is a schematic view of a portion of the apparatus of FIG. 1 illustrating geometries of the apparatus.

Referring again to FIGS. 2 and 3, apparatus 10 may further comprise detection device 32 including camera 34 and focusing lens 36. A broad area laser 38 (BAL) emits a laser beam 40 with a narrow divergence in one direction (the slow axis) and a large divergence in another direction (fast axis). Typically, the light for such lasers diverges at about 10 degrees along the slow axis and about 40 degrees along the fast axis. The slow axis and fast axis are orthogonal to each other. A fast-axis cylindrical (FAC) lens 42 is used to collimate the beam along the fast axis. The focal length and aperture of the FAC lens 42 is chosen to achieve a desired width for beam collimation along the fast axis direction. A slow-axis cylindrical (SAC) lens 44 images the source of light to a location in space. Together, these two cylindrical lenses, the FAC lens and the SAC lens, produce a generally rectangular area of illumination located at an image plane generally transverse to the direction of beam propagation. The range of converging angles along the slow axis of the beam is made to be very small as the light approaches the image plane. This can be achieved by placing a numerical aperture restricting aperture plate 46 comprising a slit-like opening S near the plane of the slow-axis cylindrical lens. Referring to FIG. 8, as an example, a plate 46 with a slit height S of 0.8 mm was used in one experiment and the SAC lens produced an image of the slit at a distance L of 146 millimeters (mm). This yields an angular range $2\phi$ in the incident beam spanning a total of ±0.157 degrees, where $\phi=\tan^{-1}((S/2)/L)$. The relationship between the depth of focus Z, the wavelength of light $\lambda$, the numerical aperture NA of the illumination and the refractive index n of the medium is found from:

$$Z=(\lambda n)/(2NA^2) \qquad (1)$$

As an example, with nominal parameters of $\lambda=800$ nanometers (nm), n=1.000 (air) and NA=sin($\phi$), the depth of focus Z for the light is 53.8 millimeters (2.1 inches). The cross-sectional height W for this line of illumination is small and was measured to be approximately 500 micrometers ($\mu$m). Hence, the illumination forms a very low numerical aperture converging sheet of light with a large depth of focus.

Figure 9:
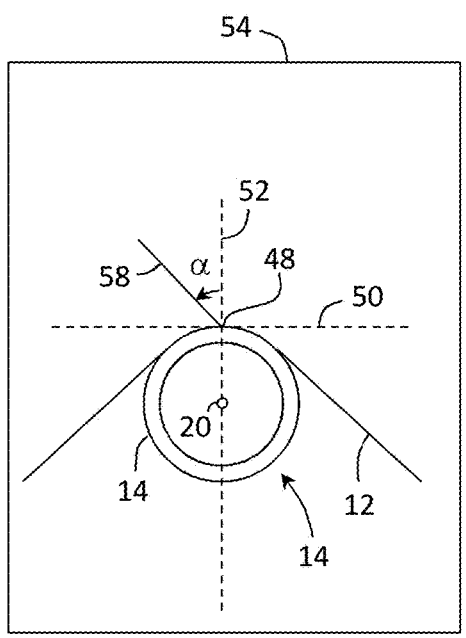
FIG. 9 is a cross sectional view of a portion of the apparatus of FIG. 2 showing reference planes.
Figure 10:
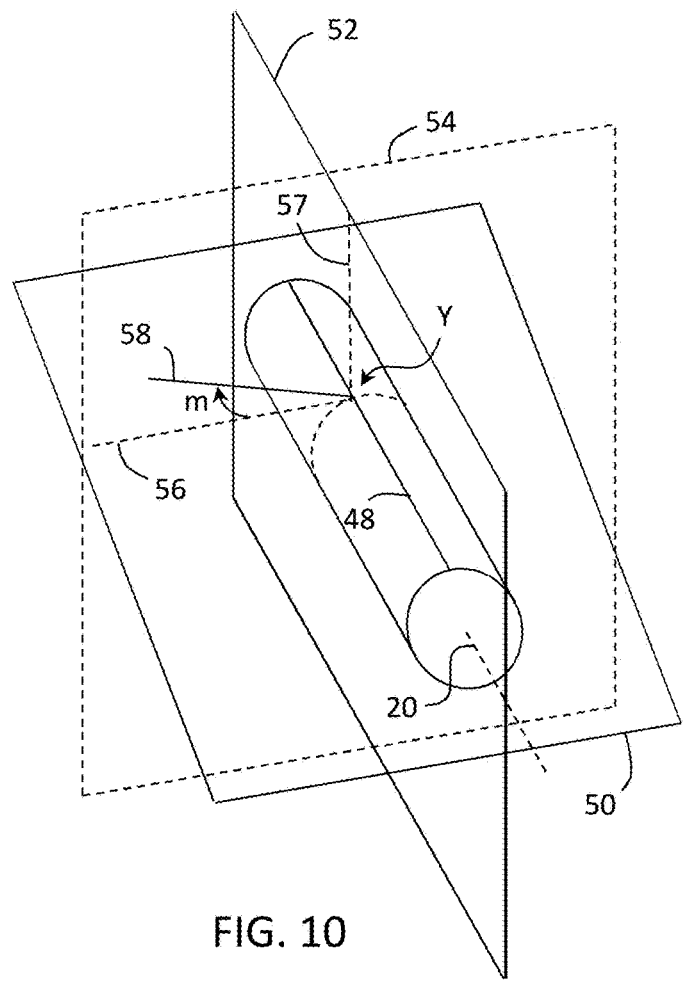
FIG. 10 is a perspective view of the portion of the apparatus of FIG. 9 showing reference planes.

This large depth of focus means the illumination can be incident on apex line 48 at a significant meridional angle and still provide uniform illumination across the apex line. As used herein, and best shown with the aid of FIGS. 9 and 10, the apex line refers to a line on that portion of glass ribbon 12 adjacent to arcuate surface 16 and including a bend, wherein a bend radius of the glass ribbon along the apex line is constant. Typically, the constant bend radius along the apex line is the minimum radius of curvature of that portion of the glass ribbon adjacent to the arcuate surface 16 of support device 14. In the simple example shown in FIGS. 9 and 10, where support device 14 is a cylinder having a circular cross section perpendicular to a longitudinal axis of the cylinder, the apex line corresponds to the line of intersection between a plane 50 tangent to the exterior of the glass ribbon 12, i.e. tangent plane 50, and a plane 52, hereinafter first azimuthal plane 52, perpendicular to tangent plane 50. In the case where arcuate surface 16 comprises a simple right circular cylinder, first azimuthal plane 52 contains entirely the longitudinal axis (e.g. axis of rotation 20) of the cylinder. As an example, in the case where the tangent plane is horizontal, the apex line is located at the top-most position on the outward facing (exterior) surface of the glass ribbon at the bend. Apex line 48 lies entirely within both tangent plane 50 and first azimuthal plane 52. As best shown in FIG. 10, a second azimuthal plane 54 is perpendicular to both first azimuthal plane 52 and tangent plane 50, and intersects apex line 48 at a point Y. The line of intersection between tangent plane 50 and second azimuthal plane 54 is a line 56 containing point Y. Line 56 lies entirely within both tangent plane 50 and second azimuthal plane 54 and is a line of intersection between planes 50 and 54. Line 57 lies entirely within second azimuthal plane 54 and is a line of intersection between second azimuthal plane 54 and first azimuthal plane 52. Both lines 56 and 57 are perpendicular to apex line 48, and to each other. Point Y is the point of intersection of planes 50, 52 and 54. Using the foregoing coordinate system described above and in FIGS. 9 and 10, and an arbitrary line 58 extending from point Y to a point in space, an azimuthal angle α can be defined and refers to an angle subtended by a line projected from line 58 onto second azimuthal plane 54, and thereafter onto first azimuthal plane 52 (e.g. line 57). A meridional angle m can be defined and refers to an angle subtended by a line projected from line 58 onto tangent plane 48, and thereafter onto second azimuthal plane 54 (e.g. line 56).

The large depth of focus and uniform illumination across apex line 48 allows the illuminating beam's meridional angle m to be set so that it exceeds the numerical aperture of the optical detection device 32. Generally, forward scattering is known from theory to be greatest between the half-angles 0° and 30°. The numerical aperture of the lens 32 in the receive system (e.g. detection device 32) that was used for testing this concept spanned half-angles of approximately 6.34°, but could be anywhere in a range from 0° to 30°. Thus, the ideal meridional angle m of the incident beam propagation for this example system should be at least marginally greater than 6.34° but less than 30°. This balances the need to reject the illuminating through-beam with the need to collect scattered light from as close to the forward angle as possible. Accordingly, the specularly reflected light and the illumination that passes over apex line 48 (the through-beam) will exceed the numerical aperture of lens 36 and will thus not be seen by the camera 34. If the meridional angle m was less than about 6.34° for this particular example, then the lens and the camera may be able see both the through-beam and the specular reflection of the light from low-angle scattering off the exterior (outward facing) surface of the glass. It can be appreciated that this reasoning supports similar optical detection device designs to be developed with different characteristics, but which yield similar results.

In use, a thin sheet (or ribbon) of glass is bent into an arch over arcuate surface 16 and oriented such that the apex line of the bend is located approximately at the center of the depth of focus Z of the illumination. The afore-mentioned illumination method ensures all of the particles along apex line 48 will receive similar illumination. In addition, the illuminating beam is oriented such that approximately one half of the width W of the illuminating beam (i.e. W/2) misses the glass entirely and approximately W/2 of the beam strikes the glass and is specularly reflected. This ensures the most intense center portion of the beam illuminates the particles at the apex line on the exterior surface $S_e$ of the glass. To be clear, the exterior surface $S_e$ of the substrate is designated in the context of that surface's position relative to arcuate surface 16. For example, for a glass substrate forming an arch over arcuate surface 16, the exterior surface $S_e$ of the substrate is that surface facing away from arcuate surface 16, whereas the interior surface $S_i$ is that surface of the glass substrate adjacent to (although spaced apart from) arcuate surface 16. It should be understood that another portion of the glass substrate may be arched in another direction, such as another adjacent arcuate surface, wherein the exterior and interior surfaces of such other portion of the ribbon may be opposite the exterior and interior surfaces of the first portion of the ribbon.

Generally, the curvature of the bend in the vicinity of the apex line will be defined by a circle of radius r. The line of illumination is directed at a 90° (or near to 90°) azimuthal angle α, as measured perpendicularly from first azimuthal plane 52 (line 57). Since the numerical aperture of the beam is so small, the width of the beam is very close to W everywhere in the vicinity of the apex along the beam path. Thus we may take this width as approximately constant and equal to W over the region where the beam strikes the substrate. Using this approximation, the range of angles θ that are incident upon the glass can be calculated from the geometry of similar triangles, as shown in FIG. 8, wherein $$A/(r-X)=X/A \tag{2}$$

$$X \approx W/2, \text{ or} \tag{3}$$

$$A^2 \approx W^*r/2 - W^2/4, \text{ and} \tag{4}$$

$$\theta = \sin^{-1}(A/r) \tag{5}$$

With a nominal roller radius r=155.6 mm (6.125 inches) and a beam width W=0.500 millimeters, A is equal to 6.23 millimeters and the subtended angle θ is equal to 2.295°. The range of angles incident on the glass over the illumination area are the same as θ (2.295°, with a mean incident angle of 90−θ/2=88.853°.

In what follows, the coherent effects of multiple reflections as the illumination reflects off the glass surface and the particles are ignored. The Fresnel transmittances through an air (n=1.000) to glass (n=1.500) interface at 88.853 degrees of incidence is 6.9% for s-polarized light and 14.9% for p-polarized light (Eq. 5-7 and FIG. 8):

$$R_s = \left\{ \frac{\left[ n_1\cos\theta_1 - n_2\sqrt{1-\left(\frac{n_1}{n_2}\sin\theta_1\right)^2} \right]}{\left[ n_1\cos\theta_1 + n_2\sqrt{1-\left(\frac{n_1}{n_2}\sin\theta_1\right)^2} \right]} \right\}^2 \tag{6}$$

$$R_p = \left\{ \frac{\left[ n_2\cos\theta_1 - n_1\sqrt{1-\left(\frac{n_1}{n_2}\sin\theta_1\right)^2} \right]}{\left[ n_2\cos\theta_1 + n_{12}\sqrt{1-\left(\frac{n_1}{n_2}\sin\theta_1\right)^2} \right]} \right\}^2 \tag{7}$$

$$\text{and, } T_{s,p} = 1 - T_{s,p}, \tag{8}$$

where T is transmittance.

After refracting through the glass, the mean propagation angle is 41.800 degrees, by Snell's Law. The incident angle on the opposite face of the glass is approximately the same, ignoring the small error due to the changing curvature of the glass radius of curvature along the beam path. Then, the transmittance through the opposite face of the glass is nearly the same as it is for the first side (6.9% for s-polarized light and 14.9% for p-polarized light). Hence, the total transmittance of optical power to particles on the opposite face of the glass is the square of the transmittance for one side, being $(6.9\%)^2$ and $(14.9\%)^2$ for s- and p-polarized light, respectively.

Figure 12:
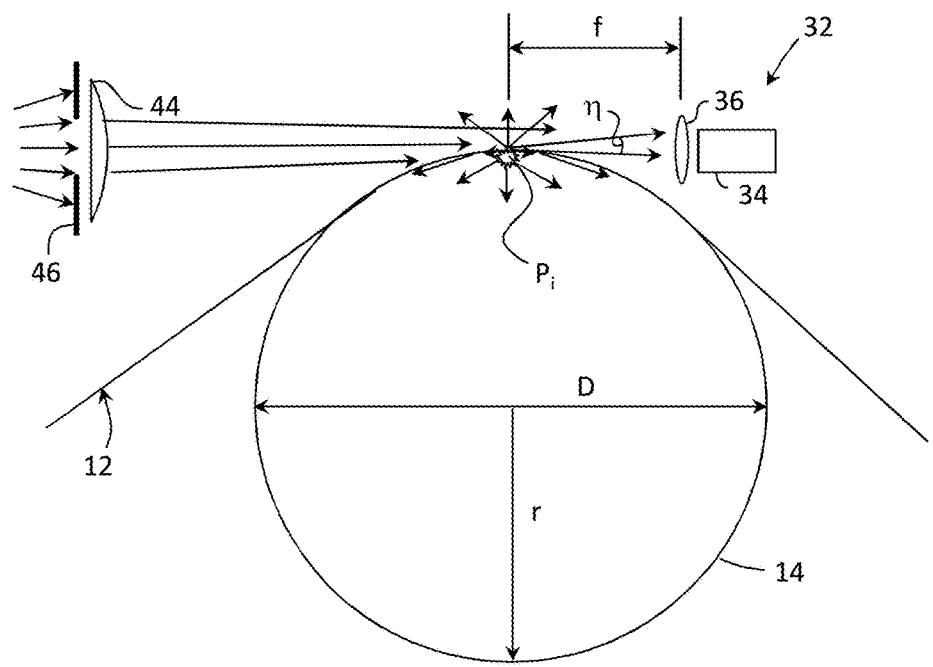
FIG. 12 is a side view of a portion of the apparatus of FIG. 2, illustrating illumination of interior surface particulate.
Figure 13:
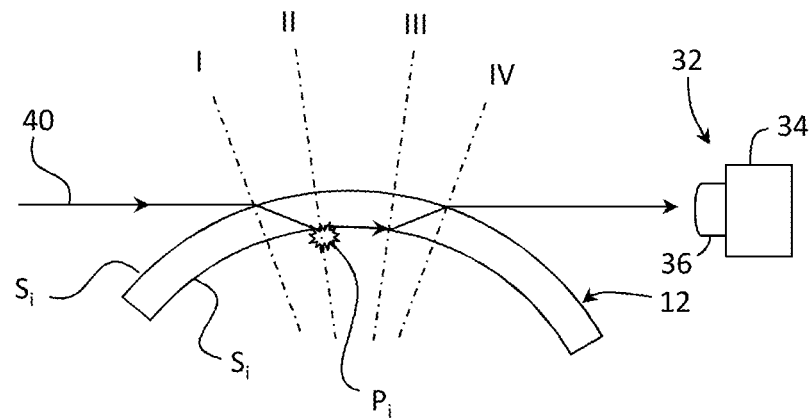
FIG. 13 is a side cross sectional view of a portion of the apparatus of FIG. 12 illustrating refraction from multiple media interfaces.

One can also consider the same effect for a "grazing detection" or "oblique detection" method. As illustrated in FIGS. 12 and 13, a detector may be placed on the same exterior side of the glass as the illumination and at a nominally large azimuthal angle α. FIG. 12 depicts the detection of scattered light from an interior particle, e.g. particle $P_i$, located on the interior surface $S_i$ of glass ribbon 12. Referring to FIG. 13, for the camera to see a particle on the interior of the bend, the light that illuminates it must pass through two interfaces with high incident angles and low transmittances. Similarly, the light that scatters from the particle must pass through two interfaces with high angles of incidence and low transmittances. Thus, light ray 40 incident on the exterior surface of glass ribbon 12 is refracted inward at air-glass interface I, and intersects glass-air interface II at particle $P_i$. Light is then forward scattered from particle $P_i$ and is refracted upon intersecting air-glass interface III. The light refracted from air-glass interface III then intersects glass-air interface IV and is directed toward detection device 32. This arrangement greatly diminishes any observable scattering from particles on the interior surface, in contrast to those on the exterior surface. The numerical aperture of the receive optics and the angle of the optical axis of the receive system will define the range of forward angles from which surface-particle scattered light can reach it. By way of example, and again referring to FIG. 12, the camera lens 36 of the system used for testing comprised a focal length F of 90 mm. The lens aperture D was 20 mm in diameter when f/# (commonly referred to as the f-stop, and is the ratio of a lens' focal length to the diameter of the entrance pupil) is the fastest (e.g. 4.5). The acceptance half angle η of the lens is equal to $\tan^{-1}(D/f)$, and equates to a lens acceptance half-angle of 6.340° for the light that exits the exterior surface. Tracing backwards from the camera, the camera could potentially receive any light that exits the glass ribbon in an angular range from 83.660° to 90.000° in angle (ignoring, for the time being, the meridonial angle of the illumination). A worst case estimate can be made for the amount of refracted power that can reach camera 34 from interior surface particles if the smallest refraction angle the camera can accept is taken to be 83.660°. Using the Fresnel equations, the TE polarized light scattering from a particle on the interior of the bend will be diminished to 32.6% at each refraction through the glass. TM polarized light will be diminished to 59.3% of its original intensity. The net effect of two surface refractions from the interior to the exterior surface is to diminish the scattered TE polarized light to $(32.6\%)^2 = 10.6\%$ and TM polarized light to $(59.3\%)^2 = 32.5\%$ of the original intensity, since refraction through two surfaces is required to reach the detector. Hence, the scattered light from a particle residing on the opposite side of the glass ribbon from the camera will be further diminished by the high reflectance incurred from the intervening surfaces between the particle and the camera.

Another factor to be considered is that particles $P_e$ on the exterior surface $S_e$ at the apex line receive additional grazing incidence illumination because the specular reflection of light from the glass substrate just in front of the particle will also strike the particle, in addition to the illumination from the light source that strikes the particle directly. Again, ignoring the curvature of the glass, the additional illumination intensity for exterior-side particles due to this first surface reflection is, by way of this example, approximately 93.1% and 85.1% for s and p-polarized light, respectively. This reflection enhancement does not occur for particles on the interior, concave side of the bend. Hence, the average net illumination of exterior-side particles is actually 1.93 times that of the incident beam itself for TE polarization and 1.85 times that of the incident beam for TM polarization.

The net discrimination of a particle residing on either side of the surface of the glass ribbon is the product of the percentage of light that strikes the particle (illumination) and the percentage of scattered light that makes it to the camera (detection). Table 1 shows that this discrimination can approach 3784:1 for TE polarized light, which is close to the dynamic range of a high quality 12-bit camera (4095 counts at 12-bits). Thus, if scattered light from a particle residing on the exterior side of the glass ribbon bend were saturating the camera pixels at, for example 4095 counts, the scattering intensity from a similar particle on the interior side of the bend would be near to or within the noise floor of the detection system. While one may consider additional reflections and transmittances within the glass sheet, or coherent effects for a more precise estimation of illumination and detection intensities, this is sufficient to illustrate one of the key side discrimination advantages of this grazing incidence illumination and grazing detection method.

Table 1 below provides a summary of the various factors that define the side discrimination capabilities of the grazing incidence and detection method of the present disclosure. A normalized incident beam intensity of 1.00 is assumed for both polarizations individually.

TABLE 1

|  | Illumination | Detection | Net Scattering Intensity | Illumination/detection gain or loss ratio |
| --- | --- | --- | --- | --- |
| Particles on Interior Surface ||||
| TE Polarization | $(6.9\%)^2$ | $(32.6\%)^2$ | 0.051% | 1961:1 loss |
| TM Polarization | $(14.9\%)^2$ | $(59.3\%)^2$ | 0.78% | 128:1 loss |
| Particles on Exterior Surface ||||
| TE Polarization | 193.1% | 100% | 193.1% | 1.93:1 gain |
| TM Polarization | 185.1% | 100% | 185.1% | 1.83:1 gain |
| Net Discrimination Ratio (Exterior/Interior) ||||
| TE Polarization ||| 3784:1 ||
| TM Polarization ||| 234:1 ||

Figure 11:
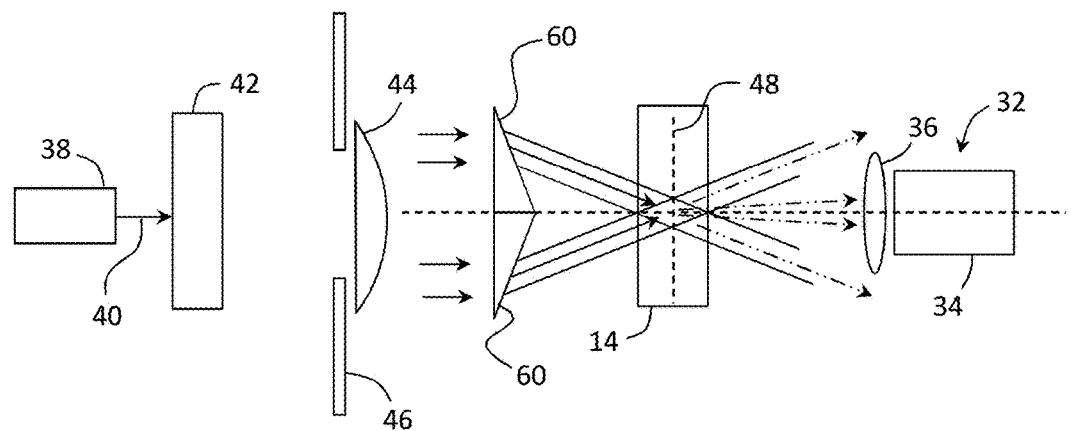
FIG. 11 is a portion of an apparatus for detecting particulate on a thin, flexible substrate according to another embodiment of the present disclosure and illustrating bidirectional illumination.

Another way to exceed the numerical aperture of camera lens 36 is to allow the initial beam from the light source to propagate with a meridional angle m of 0° (orthogonal to apex line 48) but to refract it to a larger meridional angle by using a "bypass prism" (e.g. two back-to-back angled prisms 60, such as two right-angle prisms), re-directing the light to an angle that exceeds the numerical aperture of the detection system, as shown in FIG. 11. This prevents the through-beam that misses the glass near the apex line, and the specularly reflected light, from reaching camera 34. Small angle scattering in the forward direction from particles at the apex line in front of camera 34 lies within the numerical aperture of the camera and is thus detected. The angled prisms may have a thin beam block between them to prevent multiply reflected light from reflecting inside the prisms and exiting in the direction of the substrate.

Figure 14:
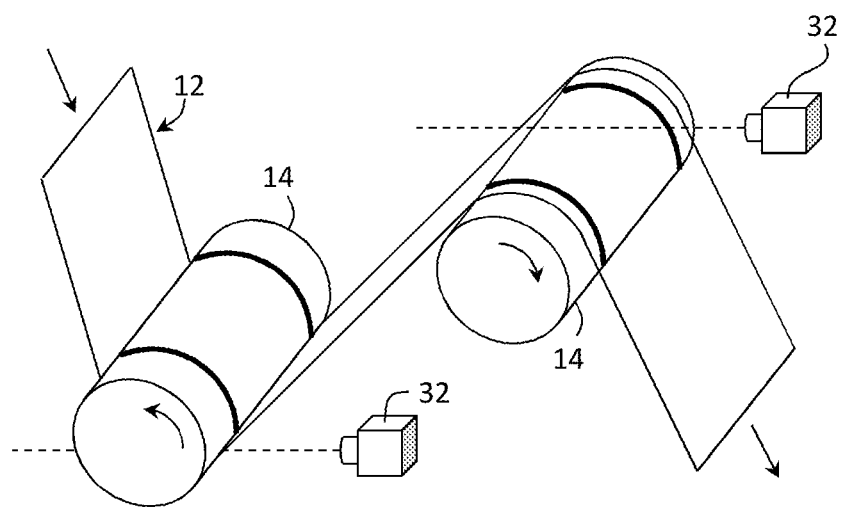
FIG. 14 is a perspective view of an apparatus for detecting particulate on a thin, flexible substrate according to another embodiment of the present disclosure wherein two surfaces of a substrate can be inspected for particulate.

FIG. 14 shows how both sides of the sheet can be inspected by using two grazing screening apparatus 10 in succession, including two support devices 14 and two detection devices 32. Each side of the glass is screened by a different detection system. For simplicity, FIG. 14 shows only the support devices, the detection devices and the glass ribbon. The second support device 14 should bend glass ribbon 12 in the opposite direction from that of the first support device such that the surface of the glass substrate that is an interior surface for one support device is an exterior surface for another support device. Backward and other scattering detection angles can be used with appropriate additional detection devices to supplement detection capabilities. The bends can also be induced on individual pieces that might be sheets of glass. The bends do not need to be as severe as is shown, just sufficient to allow placement of a detection and illumination system in the appropriate positions. One can then compare scattering signatures between the two apparatus 10 at a time interval that is equal to the ratio of the distance between the two apex line locations along the glass ribbon and the feed rate of the glass ribbon through the apparatuses. The large differences in signal intensities or the complete lack of a signal on one side of the glass ribbon and not the other side will discriminate which side the particles reside upon.

Figure 15:
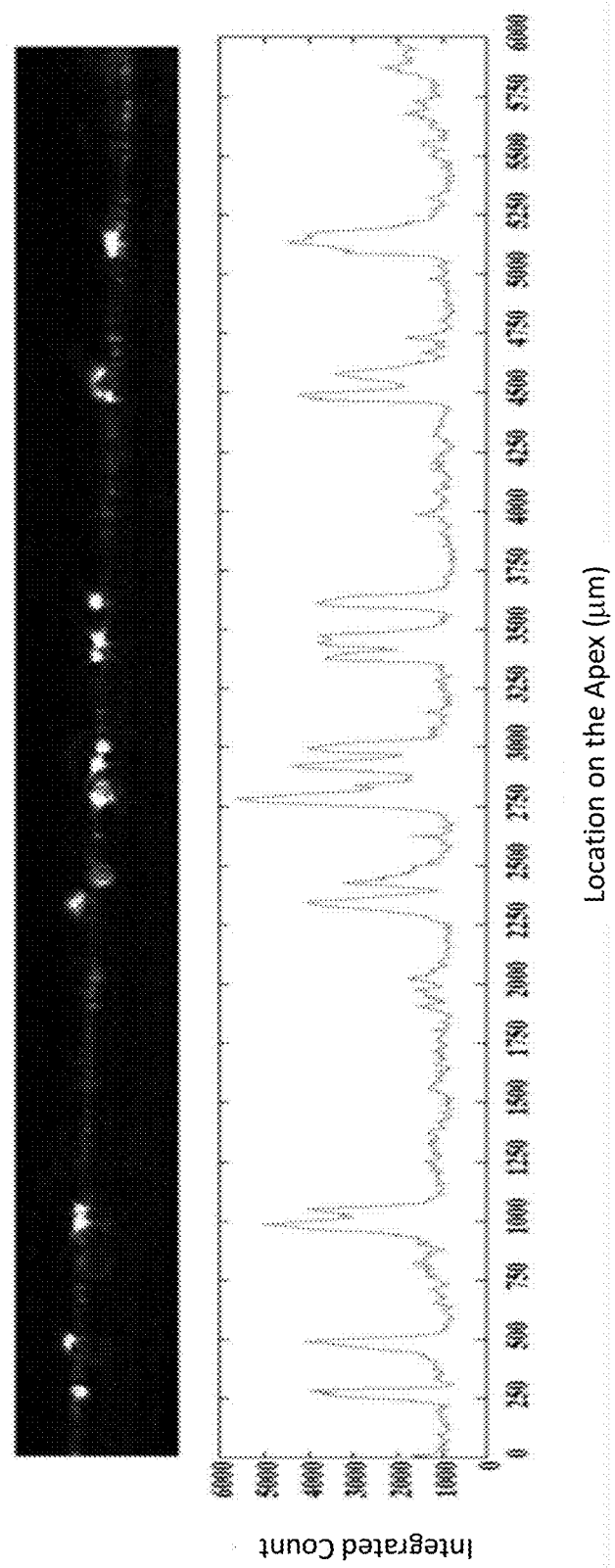
FIG. 15 is an image of illuminated particulate adjacent to a plot of the vertically integrated intensity of the image vs. horizontal position in the image corresponding to the particulate of the image.

In one experiment, a 2.54 cm×10.16 cm (1 inch×4 inch) rectangle of 100 micrometer (μm) thick flexible glass (Corning® Willow® glass) was placed in a bend over a roller. A computer was used to collect and process image data from a camera as the glass rectangle was rolled over the roller. One such image, shown in FIG. 15 both pictorially (above) and graphically (below), shows the forward scattering from prominent particles on the exterior surface of the glass substrate as the particles progress through the apex line. A region of interest was defined and integrated vertically to produce a graphical line trace of intensity for each offset position across the horizontal direction, which is parallel to the apex line. This method was chosen for expediency. It can be appreciated that any number of software packages and algorithms may be used to process the image data to obtain usable information about the particles from the image.

Figure 16:
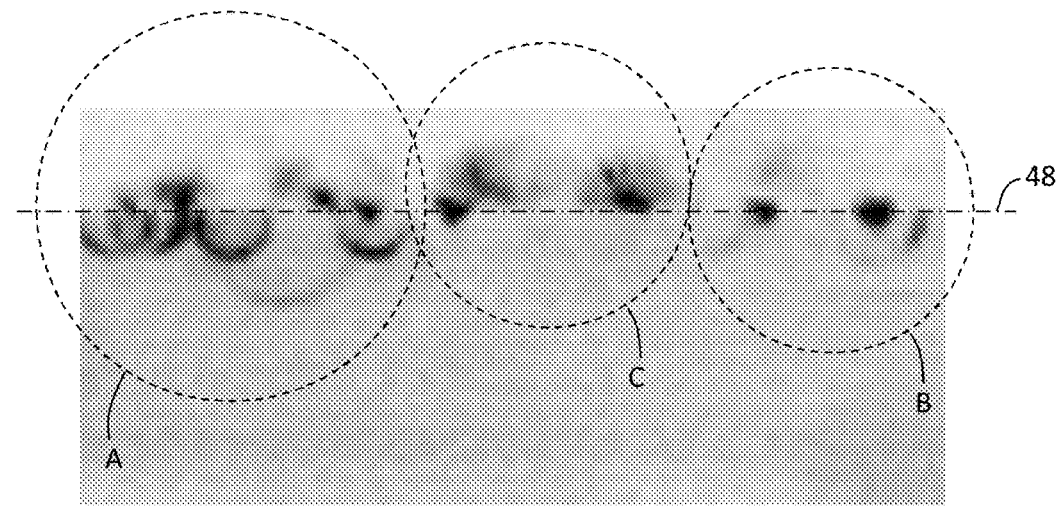
FIG. 16 is an image of illuminated particulate that are located on, before and after the apex line as it the glass is being conveyed.

There are some interesting and unique features in the camera images that are obtained while using this method as shown in FIG. 16. The image in FIG. 16 has been intentionally inverted in the grey scale to enhance viewing clarity. For example, particles that are out of focus and rising up over the tangent plane shown in region C can scatter light into the aperture of the camera, producing a half-moon of brightness that is imaged to lie above the tangent plane and apex line 48 but not below it. Any light that is scattered below the apex line from these particles cannot be seen by the camera because of the mirror-like characteristic of the glass at high angles of incidence. As the particle approaches the tangent plane (which coincides with the apex line and the focal plane of the camera), this half-moon of brightness condenses down to a point. Particles that are in focus and at the apex line appear mostly circular and straddle the tangent plane as shown in region B. When the particles are at the apex position, the scattered light will generally be the most intense and also have the smallest spatial extent as viewed by the camera. Particles that have begun to pass over the apex line and are moving downward produce a cup-like half-moon of brightness that is imaged below the tangent plane and the apex line, as shown in region A. This occurs because the top of the particle is struck by the incident beam, but not the bottom of the particle, because the light that would have struck the bottom of the particle was instead reflected by the substrate before it could reach the particle. The dynamic behavior illustrated in regions A, B and C is also an indication that the particles in this image must lie on the exterior surface.

Figure 17:
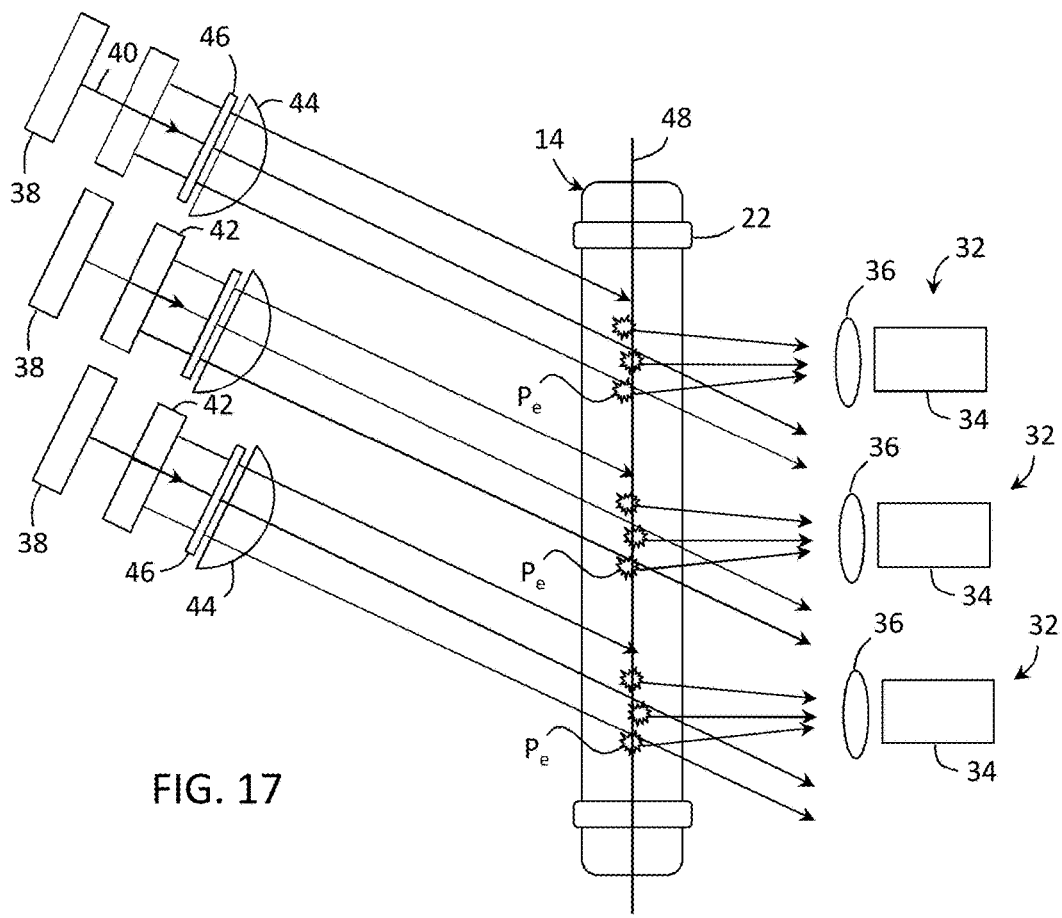
FIG. 17 is a top view of an apparatus for detecting particulate on wide expanse of a thin, flexible substrate according to an embodiment of the present disclosure.

FIG. 17 shows an apparatus for multiplexing the measurement to cover wide areas of a substrate by employing a plurality of apparatus 10 side-by-side, illuminating adjacent, exterior surfaces of the glass ribbon. The illumination and detection devices for each apparatus 10 may be mounted on removable platforms. Each apparatus 10 can then be moved to a different support device and remounted, allowing instrumentation to be ported and positioned at particular locations in the process where it might be needed.

In some embodiments a line scan camera can be used as camera 34 to increase measurement speed. Line scan cameras can be configured to capture frames in excess of 1000 frames per second. Furthermore, they typically have longer active areas (e.g., 50 millimeters) and more pixels (e.g. more than 4000) in one direction than area scan cameras do, giving them a greater width of screening coverage per camera. In addition, a cylindrical lens may be placed in front of the camera to perform the vertical integration of the image into an integrated intensity graph optically, rather than doing so by software computations. This can also decrease the number of vertical pixels necessary to capture the image of the apex region with the camera. This, in turn, decreases the camera and lens costs while simultaneously increasing detector read out rates and software processing speeds. Ultimately those modifications can lead to very high speed screening for particles that contaminate the glass sheet.

Figure 18A:
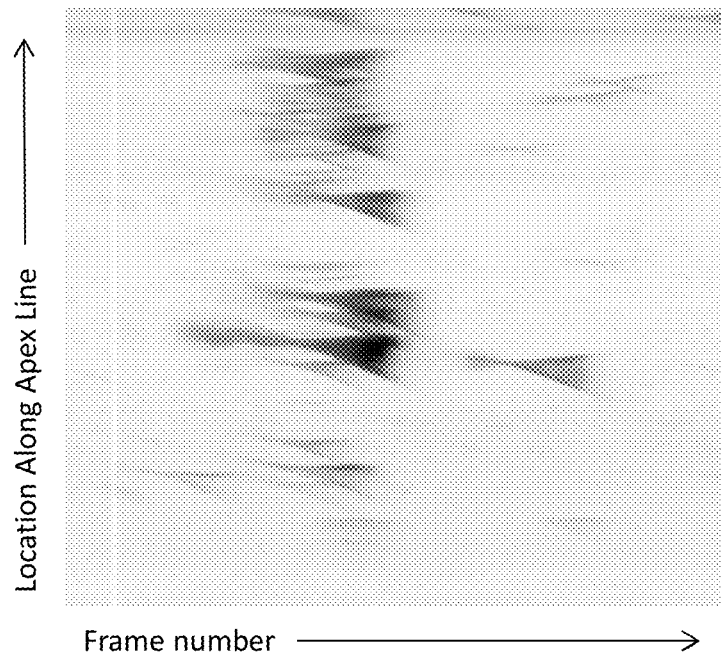
FIG. 18A and FIG. 18B are each two-dimensional integrated intensity plots vs. time as a sample with particulates on one side is being conveyed through the system, the first time with the side having the particles on the exterior of the bend (18A) and the second time having the particles on the interior of the bend (18B), illustrating the side discrimination of the described method.
Figure 18B:
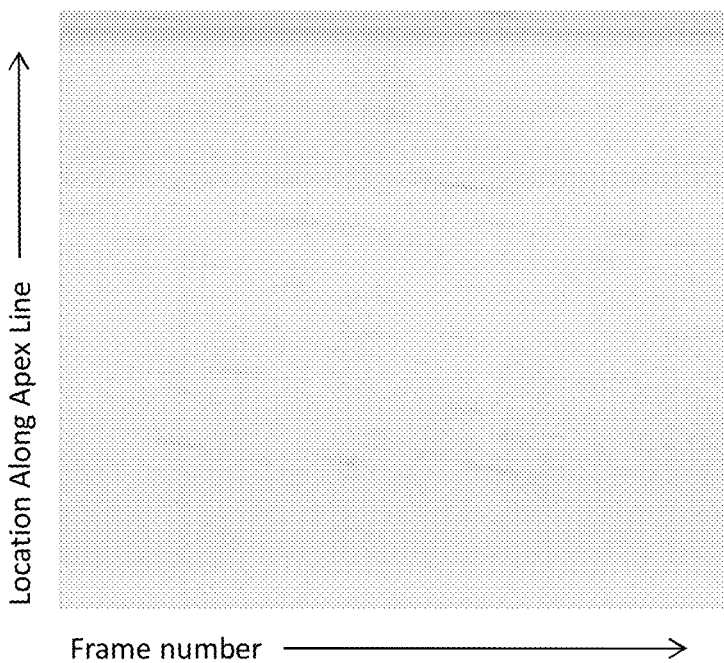

In another experiment both sides of a 2.54×10.16 centimeter thin glass substrate with a thickness of 100 micrometers were cleaned and then a line of glass particles was deposited on one side across the width of the substrate sample. Since the sample was too short to tension, a second cantilever roller was used to create the bend and the apex line in the glass. The sample was then conveyed through the detection apparatus for a total scan range of 20 millimeters in 100 micrometer steps. At each step a camera image was acquired, and the vertically integrated intensity was computed within a region of interest centered on the apex line. The exposure time and the camera gain were adjusted to produce a good image and fixed to constant values. The integrated intensities were then combined into a 2D intensity plot (FIG. 18A), where the camera image number lies on the horizontal axis, the position along the apex lies upon the vertical axis and the integrated intensity (integrated intensity count) from each camera image taken at that position is represented by image density (dark=high counts, light=low counts). Equivalently, the horizontal position could be time, assuming constant velocity. The sample was then flipped over to expose the other (clean) side of the glass as the exterior surface and then a second measurement was made on the same region of glass (FIG. 18B). The illumination, the camera exposure time and the camera gain were kept the same for both scans. Both plots use the same count-to-intensity scaling. The intensity indicates the integrated intensity and the maximum for each particle is indicative of particle size. As the images for both sides of the sample have been purposely inverted in grey scale representation for clarity, where the darker portions (greater image density) indicate greater integrated intensity of the imaged light. Large, medium and small particles could be seen when the particles were on the exterior side, as shown in FIG. 18A. However, those same particles could not be seen when the glass rectangle was flipped over and the same region was scanned as shown in FIG. 18B. Thus, the image of FIG. 18B is substantially clear. This lack of discernible image artifacts demonstrates good sample side discrimination. The length of each signal feature in the horizontal direction is also indicative of particle size. Larger particles will scatter sufficient light to be observed over a longer duration in the scan. As the particles come into the illumination, the integrated intensity ramps up until the particle crosses over the horizon at the apex. Once on the other side of the apex line, the scattered intensity drops rapidly to zero because most of the light is specularly reflected from the glass and can no longer impinge upon the particles. The precise location of each particle on the substrate can be inferred from the location where the two legs of the Y feature associated with the particle in FIGS. 18A and 18B join together.

Referring to FIG. 14, it is apparent that the image data or the integrated intensity data obtained from the first measurement system at a particular time and location in the conveyance path can be compared with the time-delayed image data or the integrated intensity data from the second measurement system further down the conveyance path, if the feed distances between them are known and the feed velocity is monitored. This comparison could further determine which side the particulates are located because the particles will be observed to be considerably brighter at one measurement system than on the other when the particles pass through the first azimuthal plane of each system, respectively. It can be appreciated that many image analysis methods other than integrated intensity could be used for processing the image data that are used in the comparison. Several, for example, might also be spatial extent on the image, pixel brightness, the number of frames in which scattered light could be observed or combinations thereof.

It will be apparent to those skilled in the art that various modifications and variations can be made to embodiments of the present disclosure without departing from the spirit and scope of the disclosure. Thus it is intended that the present disclosure cover such modifications and variations provided they come within the scope of the appended claims and their equivalents.

What is claimed is:

1. A method of detecting one or more particles on a substrate comprising:
    conveying the substrate over an arcuate surface and producing a first bend in at least a portion of the substrate
    directing a laser beam emitted by a broad area laser through a slow-axis cylindrical lens and a fast-axis cylindrical lens separate from the slow-axis cylindrical lens onto an exterior surface of the substrate at an apex line of the first bend, wherein a central axis of the laser beam is within 10 degrees of a plane tangent to the apex line, the slow-axis cylindrical lens imaging the laser beam onto an image plane transverse to a direction of the laser beam, the fast-axis cylindrical lens collimating the laser beam along a fast axis of the laser beam, the slow-axis cylindrical lens and the fast-axis cylindrical lens forming a rectangular area of illumination of the laser beam at the image plane transverse to the direction of the laser beam, and the laser beam producing scattered light from the one or more particles on the exterior surface at the apex line;
    restricting a numerical aperture of the laser beam along a fast-slow axis of the slow-axis cylindrical lens using a numerical aperture restricting aperture plate positioned between the slow-axis cylindrical lens and the fast-axis cylindrical lens; and
    detecting the scattered light with a detection device.

2. The method according to claim 1, wherein an optical axis of the detection device is within 10 degrees of the tangent plane at the apex line.

3. The method according to claim 1, wherein the conveying comprises conveying the substrate over a roller.

4. The method according to claim 3, wherein the conveying comprises contacting edge portions of the substrate with spacers positioned on the roller, the spacers configured to space the substrate above a surface of the roller.

5. The method according to claim 1, wherein the conveying comprises conveying the substrate over an air bearing to produce the first bend.

6. The method according to claim 1, wherein a meridional angle m of the central axis relative to a plane perpendicular to the apex line and within the tangent plane is in a range from greater than 0 degrees to equal to or less than 30 degrees during the directing of the laser beam.

7. The method of claim 6, wherein the meridional angle m defines a ray angle that exceeds a numerical aperture of the detection device.

8. The method according to claim 1, wherein the substrate is a glass substrate.

9. The method according to claim 8, wherein the glass substrate is a transparent glass ribbon.

10. The method according to claim 1, further comprising conveying the substrate over a second arcuate surface and producing a second bend in at least a portion of the substrate such that the exterior surface of the first bend is an interior surface of the second bend.

11. The method according to claim 1, further comprising acquiring a series of images of the scattered light during the conveying and using the images to determine at least one of locations of the particles, sizes of the particles, or the number of the particles.

12. The method according to claim 1, wherein a fast axis of the fast-axis cylindrical lens is orthogonal to a slow axis of the slow-axis cylindrical lens.

13. A method of detecting one or more particles on a surface of a glass substrate comprising:
    conveying the glass substrate over an arcuate surface and producing a first bend in at least a portion of the glass substrate;
    directing a laser beam emitted from a broad area laser through a slow-axis cylindrical lens and a fast-axis cylindrical lens separate from the slow-axis cylindrical lens onto an exterior surface of the glass substrate at an apex line of the first bend, wherein a central axis of the laser beam is within 10 degrees of a plane tangent to the apex line, the slow-axis cylindrical lens imaging the laser beam onto an image plane transverse to a direction of the laser beam, the fast-axis cylindrical lens collimating the laser beam along a fast axis of the laser beam, the slow-axis cylindrical lens and the fast-axis cylindrical lens forming a rectangular area of illumination of the laser beam at the image plane transverse to the direction of the laser beam, and the laser beam produces scattered light from the one or more particles on the exterior surface at the apex line; and
    restricting a numerical aperture of the laser beam along a fast-slow axis of the slow-axis cylindrical lens using a numerical aperture restricting aperture plate positioned between the slow-axis cylindrical lens and the fast-axis cylindrical lens; and
    detecting the scattered light with a detection device.

14. The method according to claim 13, wherein an optical axis of the detection device is within 10 degrees of the tangent plane at the apex line.

15. The method according to claim 13, wherein the glass substrate is a glass ribbon and the conveying comprises unspooling the glass ribbon from a spool prior to the directing.

16. The method according to claim 13, wherein the glass substrate is a glass ribbon and the conveying comprises spooling the glass ribbon onto a spool after the directing.

17. The method according to claim 13, wherein the glass substrate is a glass ribbon and the conveying comprises conveying the glass substrate over a second arcuate surface and producing a second bend in at least a portion of the glass substrate such that the exterior surface of the first bend is an interior surface of the second bend.

18. The method according to claim 17, further comprising illuminating an exterior surface of the glass ribbon at an apex line of the second bend with a second laser beam, wherein a central axis of the second laser beam is within 10 degrees of a plane tangent to the apex line of the second bend and the second laser beam is elongated in a direction perpendicular to the central axis of the second laser beam, the illuminating producing scattered light from the one or more particles on the exterior surface of the second bend at the apex line of the second bend.

* * * * *

UNITED STATES PATENT AND TRADEMARK OFFICE
CERTIFICATE OF CORRECTION

PATENT NO. : 9,588,056 B2  
APPLICATION NO. : 14/722478  
DATED : March 7, 2017  
INVENTOR(S) : Norman Henry Fontaine et al.

Page 1 of 1

It is certified that error appears in the above-identified patent and that said Letters Patent is hereby corrected as shown below:

In the Claims

Column (17), Claim 1, Line 23:
Change "fast-slow axis", to
-- slow axis -- therefor.

Column (18), Claim 13, Line 23:
Change "fast-slow axis", to
-- slow axis -- therefor.

Signed and Sealed this
Twenty-fourth Day of April, 2018

Andrei Iancu
*Director of the United States Patent and Trademark Office*